US012594378B2

(12) United States Patent
Mojarrad et al.

(10) Patent No.:  US 12,594,378 B2
(45) Date of Patent:       Apr. 7, 2026

(54) PRESSURE RELIEF VALVE FOR DRUG DELIVERY DEVICE

(71) Applicant: AMGEN INC., Thousand Oaks, CA (US)

(72) Inventors: Mehran Mojarrad, Thousand Oaks, CA (US); Ali Nekouzadeh, Simi Valley, CA (US); Scott R. Gibson, Simi Valley, CA (US); Sheldon Moberg, Thousand Oaks, CA (US); Paul Daniel Faucher, Escondido, CA (US)

(73) Assignee: AMGEN INC., Thousand Oaks, CA (US)

( * ) Notice: Subject to any disclaimer, the term of this patent is extended or adjusted under 35 U.S.C. 154(b) by 882 days.

(21) Appl. No.: 17/626,667

(22) PCT Filed: Jul. 16, 2020

(86) PCT No.: PCT/US2020/042220
    § 371 (c)(1),
    (2) Date: Jan. 12, 2022

(87) PCT Pub. No.: WO2021/011714
    PCT Pub. Date: Jan. 21, 2021

(65) Prior Publication Data
    US 2022/0288305 A1      Sep. 15, 2022

Related U.S. Application Data

(60) Provisional application No. 62/875,813, filed on Jul. 18, 2019.

(51) Int. Cl.
    *A61M 5/142*      (2006.01)
    *A61M 5/145*      (2006.01)

(52) U.S. Cl.
    CPC .... *A61M 5/14526* (2013.01); *A61M 5/14248* (2013.01); *A61M 5/14593* (2013.01); *A61M 2005/14252* (2013.01); *A61M 2205/3337* (2013.01)

(58) Field of Classification Search
    CPC .......... A61M 5/14526; A61M 5/14248; A61M 5/14593; A61M 2005/14252;
    (Continued)

(56) References Cited

U.S. PATENT DOCUMENTS

| | | | | | |
|---|---|---|---|---|---|
| 7,008,403 | B1 * | 3/2006 | Mallett | ................... | G01F 11/04 604/131 |
| 7,947,017 | B2 * | 5/2011 | Edwards | ............. | A61M 5/2046 604/140 |

(Continued)

FOREIGN PATENT DOCUMENTS

| | | |
|---|---|---|
| WO | WO-2018164829 A1 | 9/2018 |
| WO | WO-2019032482 A2 | 2/2019 |

OTHER PUBLICATIONS

International Search Report and Written Opinion of PCT/US2020/042220, dated Oct. 9, 2020.

*Primary Examiner* — Kevin C Sirmons
*Assistant Examiner* — William R Frehe
(74) *Attorney, Agent, or Firm* — MARSHALL, GERSTEIN & BORUN LLP; Michael P. Furmanek

(57) ABSTRACT

A drug delivery device includes a housing releasably coupled with a patient, a pressure chamber disposed in the housing and including a vent, a container at least partially disposed in the pressure chamber for storing a drug connectable in fluid communication with a fluid conduit, an activation mechanism, and a relief mechanism. The activation mechanism releases a pressurized drive fluid into the pressure chamber for expelling the drug from the container into the fluid conduit. The relief mechanism is operably (Continued)

coupled to the fluid conduit and is adapted to open the vent to release the drive fluid from the pressure chamber in response to a predetermined condition.

9 Claims, 5 Drawing Sheets

(58) Field of Classification Search
CPC .... A61M 2005/247; A61M 2005/2474; A61M 5/14244; A61M 5/2046; A61M 5/2053; A61M 2205/3337
See application file for complete search history.

(56) References Cited

U.S. PATENT DOCUMENTS

| 9,517,307 | B2 * | 12/2016 | Blondino | A61M 5/2053 |
|---|---|---|---|---|
| 2008/0058719 | A1 * | 3/2008 | Edwards | A61M 5/2033 |
| | | | | 604/140 |
| 2008/0147007 | A1 * | 6/2008 | Freyman | A61M 5/14593 |
| | | | | 604/151 |
| 2009/0247940 | A1 * | 10/2009 | Williamson | A61M 5/30 |
| | | | | 604/70 |
| 2013/0110050 | A1 * | 5/2013 | Boyd | A61M 5/24 |
| | | | | 604/191 |
| 2013/0184640 | A1 * | 7/2013 | Li | A61M 5/172 |
| | | | | 604/67 |
| 2013/0184641 | A1 * | 7/2013 | Li | A61M 5/172 |
| | | | | 604/67 |
| 2017/0182243 | A1 * | 6/2017 | Cole | A61M 5/14248 |
| 2019/0111205 | A1 * | 4/2019 | Kim | A61M 5/1452 |
| 2019/0192775 | A1 * | 6/2019 | Kim | A61M 5/3146 |

* cited by examiner

PRESSURE RELIEF VALVE FOR DRUG DELIVERY DEVICE

CROSS-REFERENCE TO RELATED APPLICATION

This is the United States national phase of International Patent Application No. PCT/US20/42220, filed on Jul. 16, 2020, which claims the priority benefit of U.S. Provisional Application No. 62/875,813, filed on Jul. 18, 2019, the entire contents of each of the foregoing being hereby incorporated by reference herein.

FIELD OF DISCLOSURE

The present disclosure generally relates to drug delivery devices and, more particularly, mechanisms and methods for relieving accumulated pressure in drug delivery devices.

BACKGROUND

Drug delivery devices, such as injectors, are used to deliver liquid drugs to a patient. Upon activation, drug delivery devices expel a drug stored within an internal reservoir of a container through a needle, cannula, or other delivery member into the patient.

Viscous drugs, including some biologics, can require substantial forces to expel the drug from the reservoir, and thus may have longer injection times. As higher viscosity drugs are delivered via drug delivery devices, requisite driving forces needed to dispense the drug must also increase. These driving forces may be generated by pressurized gas mechanisms that come into direct contact with components of the container that contains the drug. In some approaches, containers may be disposed in pressure chambers that can assist in reducing forces exerted on the container during drug administration. Upon completion of the drug administration process, residual pressure may remain within the pressure chamber and pose a safety risk.

As described in more detail below, the present disclosure sets forth systems for delivery devices embodying advantageous alternatives to existing systems and methods, and that may address one or more of the challenges or needs mentioned herein, as well as provide other benefits and advantages.

SUMMARY

In accordance with a first aspect, a drug delivery device includes a housing releasably coupled with a patient, a pressure chamber disposed in the housing and including a vent, a container at least partially disposed in the pressure chamber for storing a drug connectable in fluid communication with a fluid conduit, an activation mechanism, and a relief mechanism. The activation mechanism releases a pressurized drive fluid into the pressure chamber for expelling the drug from the container into the fluid conduit. The relief mechanism is operably coupled to the fluid conduit and is adapted to open the vent to release the drive fluid from the pressure chamber in response to a predetermined condition. In some examples, the predetermined condition may be a change in pressure in the fluid conduit. In other examples, the predetermined condition may be exceeding a pressure threshold. In some examples, the movable member is in the form of a fluid piston and/or a diaphragm. The pressurized drive fluid may be in the form of a pressurized gas and/or a pressurized liquid.

In some examples, the relief mechanism includes a relief chamber having a first end and a second end. The relief chamber is operably coupled to the fluid conduit and includes a movable member movable between the first end and the second end thereof. The movable member is biased towards the first end of the relief chamber. In some examples, a resilient member is coupled to the movable member to bias the movable member towards the first end of the relief chamber.

In some examples, upon engaging the activation mechanism, the drug urges the movable member from a storage state to a first operational state where the movable member moves to the second end of the relief chamber to operably couple the relief mechanism to the vent. Upon completion of drug delivery, the movable member moves towards the first end of the relief chamber and engages the vent to remove the drive fluid from the pressure chamber.

In some examples, the drug delivery device may further include a container access mechanism at least partially disposed within the housing that is operably coupled to at least one of the pressure chamber or the container. The container access mechanism includes a needle or a cannula and a sterile barrier disposed proximal to the needle or cannula in a first configuration where the sterile barrier is intact. Upon engaging the activation mechanism, relative movement between the needle or cannula and the sterile barrier causes the needle or cannula to pierce the sterile barrier to create the fluid conduit allowing the medicament to be expelled from the container.

In some approaches, the drug delivery device can include an overpressure relief mechanism that is operably coupled to the relief mechanism to release the drive fluid from the pressure chamber when a pressure within the pressure chamber exceeds a predetermined value. The overpressure relief mechanism includes a resilient member adapted to exert an opposing urging force on the relief valve.

In accordance with a second aspect, a pressure relief mechanism for a drug delivery device having a pressure chamber, a container, and a fluid conduit includes a relief chamber, a movable member, and a vent. The relief chamber is connected in fluid communication with the container via the fluid conduit. The movable member is adapted to move within the relief chamber in response to a predetermined condition. The vent is selectively openable by the movable member to release pressure from the pressure chamber.

BRIEF DESCRIPTION OF THE DRAWINGS

The above needs are at least partially met through provision of the pressure relief valve for a drug delivery device described in the following detailed description, particularly when studied in conjunction with the drawings, wherein.

The accompanying figures show embodiments according to the disclosure and are exemplary rather than limiting.

US 12,594,378 B2

3

Figure 1:
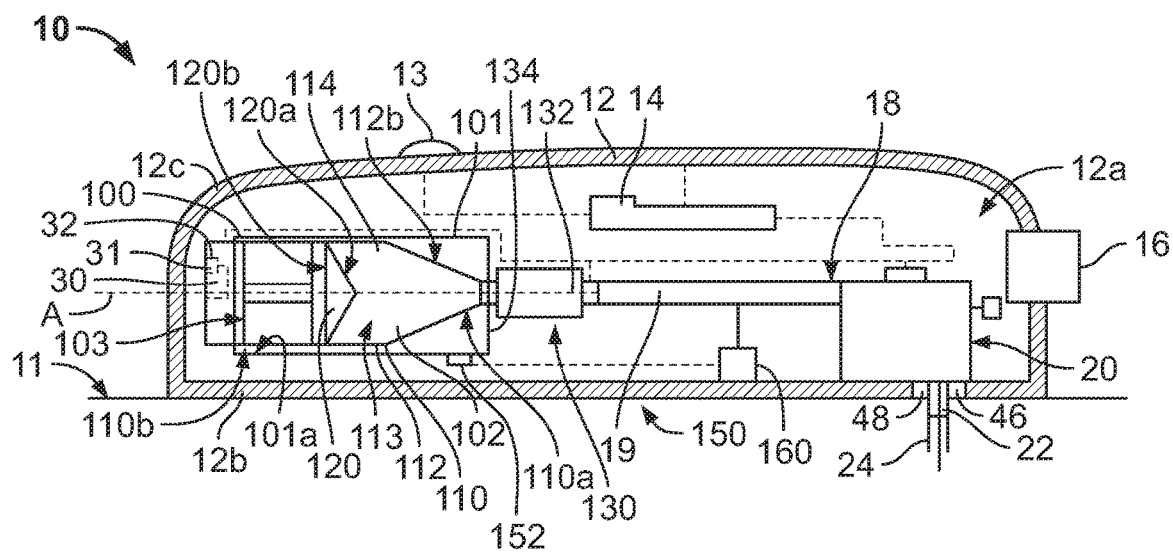
FIG. 1 illustrates a schematic representation of an example arrangement of a drug delivery device having a pressure relief arrangement in accordance with various embodiments.
Figure 2:
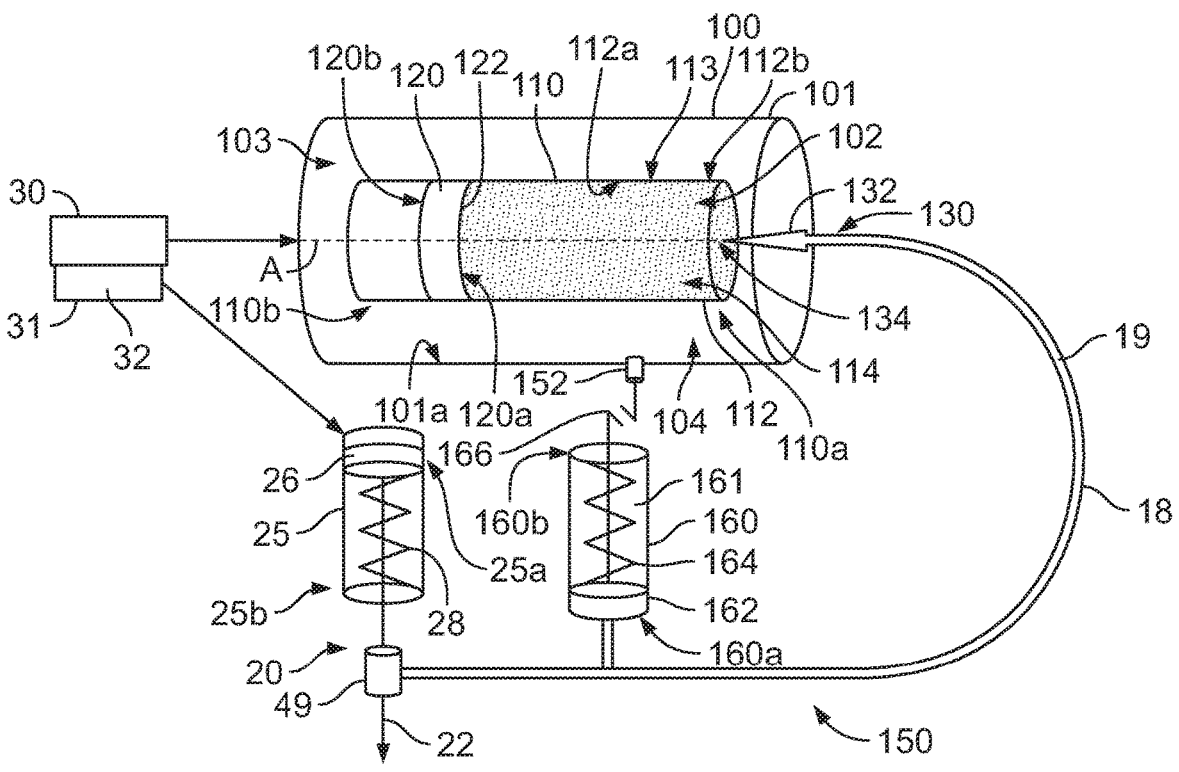
FIG. 2 illustrates a schematic representation of a first example pressure relief mechanism for the example drug delivery device of FIG. 1 in a storage state in accordance with various embodiments.
Figures 3, 4:
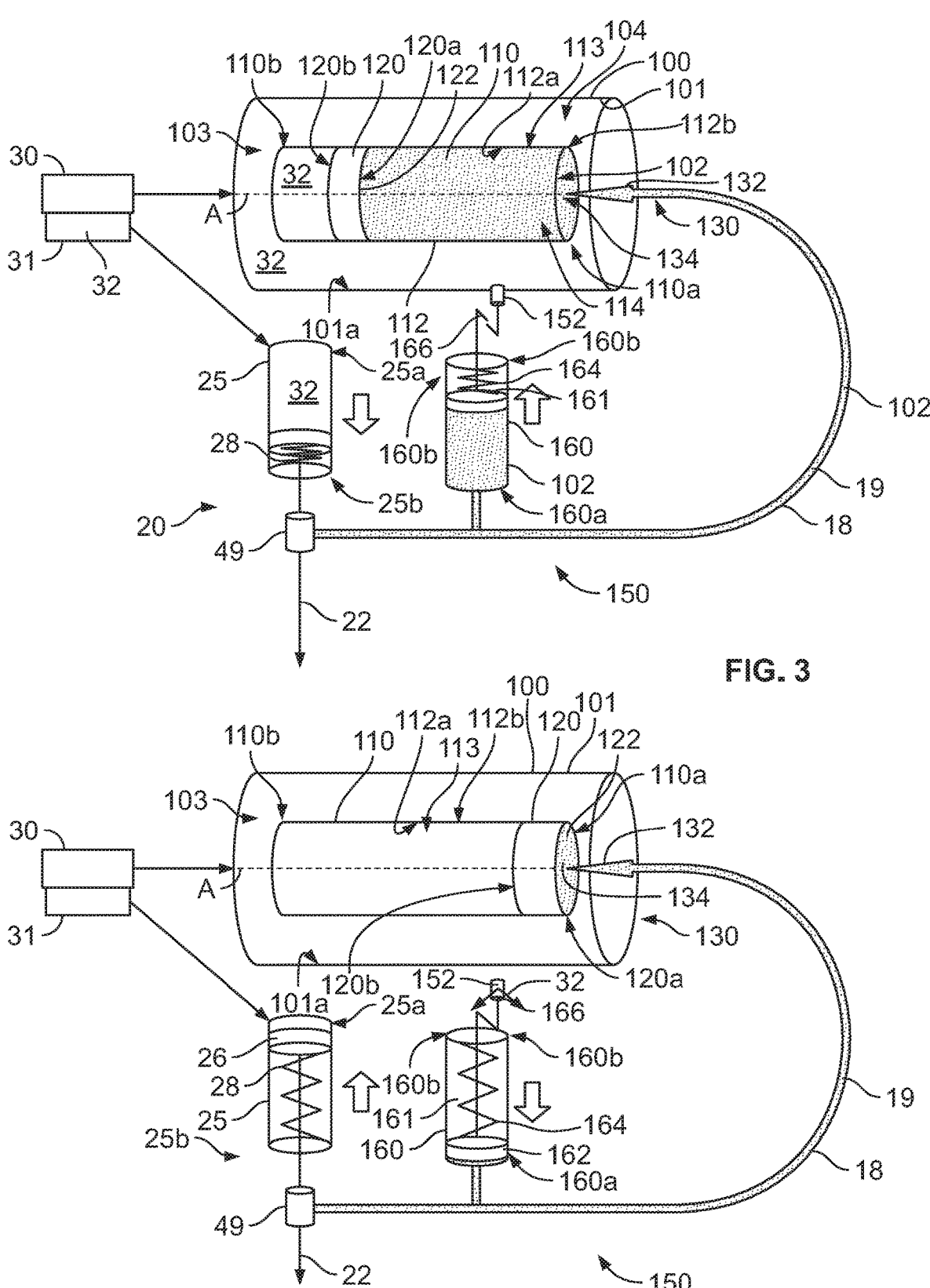
FIG. 3 illustrates a schematic representation of the first example pressure relief mechanism of FIG. 2 in a first operational state in accordance with various embodiments.
Figure 5:
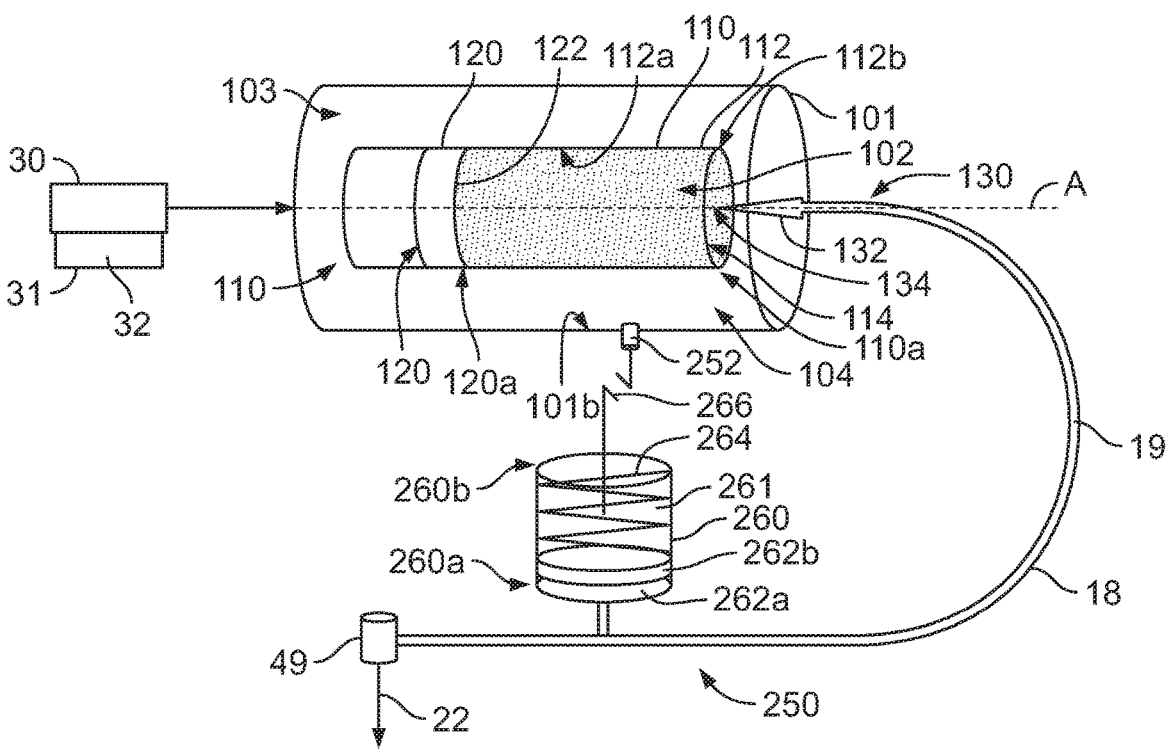
Figure 6:
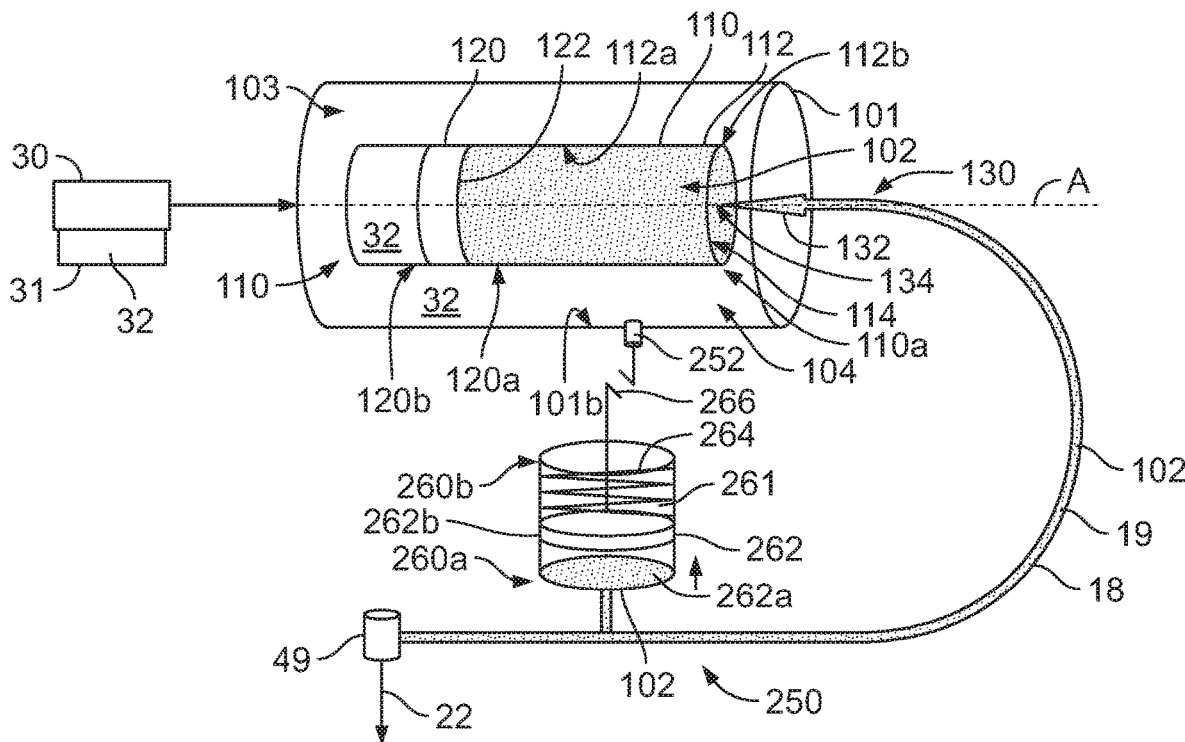
Figure 7:
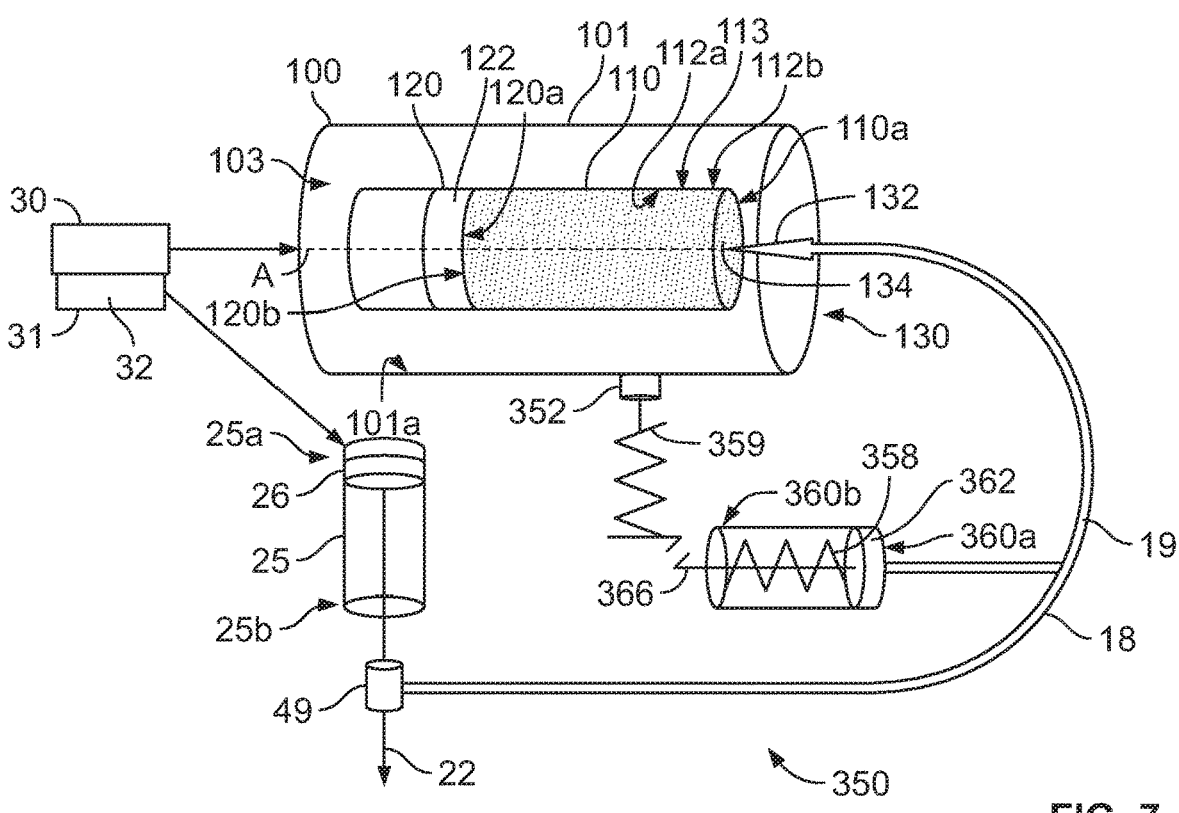
Figure 8:
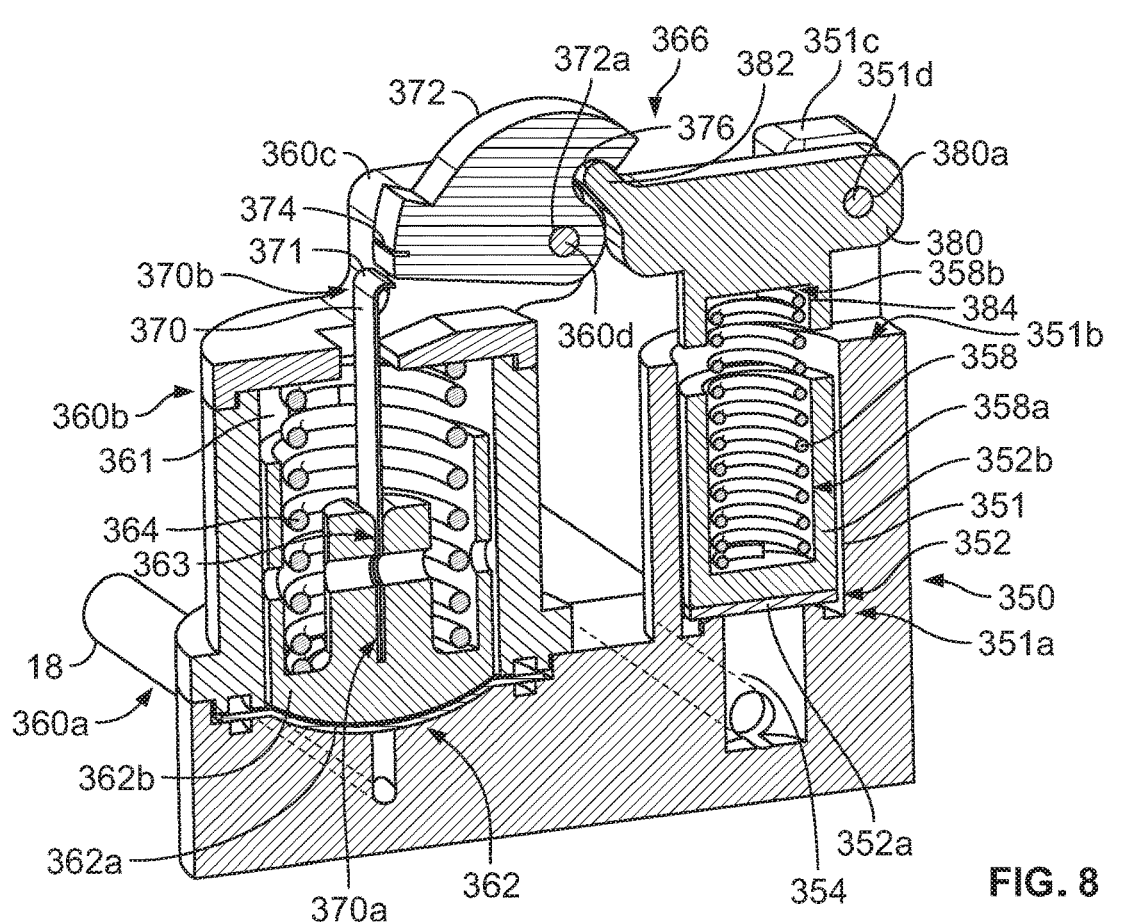
Figures 9, 10:
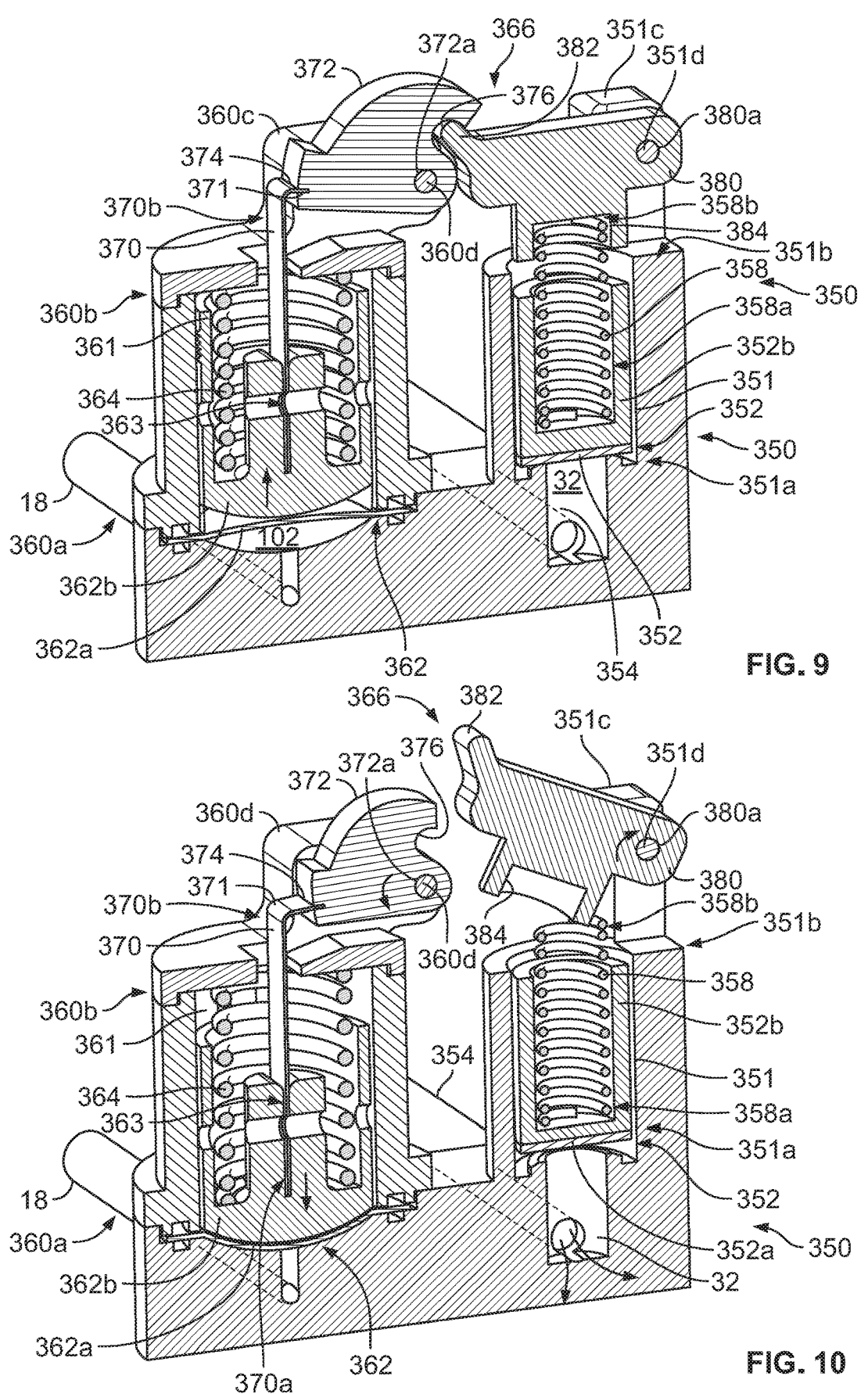

FIG. 4 illustrates a schematic representation of the first example pressure relief mechanism of FIGS. 2 and 3 upon completion of drug delivery in accordance with various embodiments;

FIG. 5 illustrates a schematic representation of a second example pressure relief mechanism for the example drug delivery device of FIG. 1 in a storage state in accordance with various embodiments;

FIG. 6 illustrates a schematic representation of the second example pressure relief mechanism of FIG. 5 in a first operational state in accordance with various embodiments;

FIG. 7 illustrates a schematic representation of a third example pressure relief mechanism for the example drug delivery device of FIG. 1 having an overpressure relief mechanism in accordance with various embodiments;

FIG. 8 illustrates a detailed schematic representation of the third example pressure relief mechanism of FIG. 7 in a storage state in accordance with various embodiments;

FIG. 9 illustrates a detailed schematic representation of the third example pressure relief mechanism of FIGS. 7 and 8 in a first operational state in accordance with various embodiments; and FIG. 10 illustrates a detailed schematic representation of the third example pressure relief mechanism of FIGS. 7-9 upon completion of drug delivery in accordance with various embodiments.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to a drive system for a drug delivery device that includes a pressure relief arrangement. The drug delivery device may include a housing defining a shell and an inner volume, a drive system, a pressure chamber including a vent, a container including a reservoir filled or adapted to be filled with a drug, an insertion mechanism, an activation mechanism, a fluid flow connection, and a relief mechanism, each of which is at least partially disposed within the housing. The drive system is driven via a drive fluid (e.g., a pressurized gas and/or a pressurized liquid) that when released exerts a force to expel the drug from the container through the fluid flow connection. The relief mechanism is responsive to a change in pressure in the fluid flow connection to open the vent to release the drive fluid from the pressure chamber.

Referring to the Figures, a general drug delivery device 10 is provided that may include any number of aspects of the pressure relief arrangement herein described. In some embodiments, including the one illustrated in FIG. 1, the drug delivery device 10 may be configured as a wearable drug delivery device, such as an on-body injector or an ambulatory infusion pump, that may be releasably coupled with a patient (e.g., to a patient's tissue 11 such as the patient's skin) to administer delivery of a drug treatment. In other embodiments, the drug delivery device 10 may be in the form of an autoinjector, a pen injector, or any other type of handheld devices including hybrids thereof. The drug delivery device 10 may be operated to subcutaneously or transdermally deliver a drug to a patient. The drug delivery device 10 may be configured to automatically deliver a fixed or a patient/operator-settable dose of a drug over a controlled or selected period of time. The drug delivery device 10 may be intended for self-administration by the patient, but may also be used by a caregiver or a formally trained healthcare provider to administer an injection.

The drug delivery device 10 has a housing 12 that is releasably coupled with the patient's tissue 11 and that defines a shell having an inner volume 12a, a needle insertion mechanism 20, an activation mechanism 30, a pressure chamber 100, a container 110 (which, in some examples, may be referred to as a primary container), a plunger 120, a container access mechanism 130, and a pressure relief system 150, each of which may be at least partially disposed within the housing 12. It is appreciated that the releasable coupling between the housing 12 and the patient's skin 11 can include any coupling or couplings that allow the drug delivery device 10 to be selectively secured to the patient, including the user holding the device 10 against the injection site, a suction force, an adhesive, or other force holding the device 10 to the patient. Further, the drug delivery device may include a controller 14, an actuator 16 (e.g., a depressible button) that is arranged on an exterior of the housing 12, and a fluid conduit 18.

The container 110 has a wall 112 that includes an interior surface 112a defining an interior volume 113. The plunger 120 is moveably disposed within the container 110 and has a first end 120a and a second end 120b. The first end 120a of the plunger 120 includes an interior surface 122. The interior surface 112a of the container 110 and the interior surface 122 of the plunger 120 define a reservoir 114 that contains a drug 102.

Generally, the pressure relief system 150 includes a vent 152 coupled to the pressure chamber 100 and a relief chamber 160 in fluid communication with the container 110 via the fluid conduit 18. As will be discussed in further detail below, the vent 152 is selectively openable to release a drive fluid 32 from the pressure chamber 100 in response to a predetermined condition such as a change in pressure in the fluid conduit 18 and/or when a pressure threshold is exceeded. It is appreciated that the predetermined condition may also include any other event that warrants a venting event.

The housing 12 may include a bottom wall 12b to be releasably coupled (e.g., adhered with an adhesive) with the patient's skin 11, and a top wall 12c including one or more visual feedback mechanisms 13 such as, for example a window, an opening, and/or an illumination system (not illustrated) for viewing the container 110 and the drug 102 contained therein. The one or more visual feedback mechanisms 13 may be used to communicate information to the user about the operational state of the drug delivery device 10 and/or the condition of the medicament or drug 102. An opening 46 may be formed in the bottom wall 12b, and optionally a pierceable sterile barrier or septum 48 may extend across the opening 46 to seal the interior of the housing 12 prior to use. In some embodiments, the pierceable sterile barrier 48 may be omitted, and instead a removable sealing member (not illustrated) may cover and seal closed the opening 46 prior to use. The exterior of the needle insertion mechanism 20 may be defined by an insertion/retraction mechanism housing that is separate from the housing 12.

The fluid conduit 18 connects the container 110 to the needle insertion mechanism 20 and the relief chamber 160. The actuator 16 is configured to initiate operation of the drug delivery device 10 by activating, via mechanical and/or electrical means (shown in dotted lines in FIG. 1), the activation mechanism 30, the needle insertion mechanism 20, the controller 14, and/or other mechanisms and/or electronics. In some examples, wireless communication may be employed to cause the device 10 to be activated. In embodiments where the actuator 16 is a button that is depressed or otherwise physically moved by a user or patient, the actuator 16 may be configured to exert a motive force needed to activate the needle insertion mechanism 20, the fluid pathway connector 18, the activation mechanism 30, the controller 14, and/or other mechanisms. In such embodiments, the actuator 16 may be physically connected to, either directly or indirectly via a mechanical linkage, the needle insertion mechanism 20, the activation mechanism 30, the fluid pathway connector 18, and/or other mechanisms such that manually depressing or otherwise interacting with the actuator 16 supplies the motive force necessary to activate the needle insertion mechanism 20, the activation mechanism 30, the fluid pathway connector 18, and/or other mechanisms.

The fluid conduit 18 defines a sterile fluid flow path 19 between the container 110 and the needle insertion mechanism 20. The container access mechanism 130 is coupled to the fluid conduit 18 and is configured to insert a container needle 132 through a septum 134 associated with and/or covering the container 110 to establish fluid communication between the container 110 and the sterile fluid flow path 19 in response to activation of the drug delivery device 10, for example, via the actuator 16. In the illustrated examples, relative movement between the container 110 and the container access mechanism 130 causes the container needle 132 to pierce the septum 134. In some examples, the container needle 132 may be staked to the container 110 such that the container needle 132 cannot move relative to the wall 112 of the container 110; whereas, in other examples, the container needle 132 may be moveable relative to the container 110 and may access the reservoir 114 of the container 110 by piercing through the septum 134 during operation or set up the drug delivery device 10. In some examples, the needle insertion mechanism 20 and the container 110 and/or other components of the drive system 100 such as the container access mechanism 130 may be integrated into a single unit, and thus the fluid conduit 18 may not be included in the drug delivery device 10.

For example, in some embodiments, manually depressing or otherwise moving the actuator 16 may cause the fluid conduit 18 and the container access mechanism 130 to move towards the container 110, or cause the container 110 to move towards the fluid conduit 18 and the container access mechanism 130, and thereby cause the container needle 132 to penetrate through the seal member or septum 134, thereby creating the fluid flow path between the reservoir 114 and the fluid flow path 19. In some examples, the container 110 and the container access mechanism 130 may have corresponding coupling mechanisms such as annular protrusions and corresponding grooves (not shown) that selectively secure the container 110 and the container access mechanism 130 in a fluidly coupled or decoupled configuration.

Additionally, or alternatively, the actuator 16 may operate as an input device that transmits an electrical and/or mechanical signal to the controller 14, which in turn may execute programmable instructions to control operation of the needle insertion mechanism 20, the activation mechanism 30, the fluid pathway connector 18, and/or other mechanisms. In such embodiments, the controller 14 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 16 and which, in response to an electrical control signal received from the controller 14, exerts the motive force needed to activate the needle insertion mechanism 20, the activation mechanism 30, the fluid pathway connector 18, and/or other mechanisms.

The activation mechanism 30 may include any number of components and/or sub-components to cause a drive fluid 32 to drive, urge, and/or exert a force on the plunger 120 to cause the drug or medicament 102 stored therein to be dispensed therefrom. In some examples, the drive fluid 32 may be a compressed $CO_2$ gas or other compressed gas and/or a compressed liquid which is initially stored within a pressure vessel or other container 31, and the activation mechanism 30 may be configured to release the compressed gas and/or liquid from the pressure vessel or other container 31 by opening a valve, which allows the compressed gas and/or liquid to flow into the container 110. In other examples, the activation mechanism 30 may be in the form of a hydro-pneumatic actuation system whereby a hydraulic and/or pneumatic force is exerted on the drive fluid 32 to move the plunger 120 through the container 110 to expel the drug 102 therefrom. In other examples, the activation mechanism 30 may include any number of resilient members (e.g., springs) that exert an urging force on the drive fluid 32. Examples of suitable activation mechanisms 30 are described in U.S. App. No. 62/543,058, filed on Aug. 9, 2017, the entire contents of which are incorporated by reference herein. Other examples of suitable activation mechanisms 30 are possible. In any of these examples, the activation mechanism 30 may additionally be coupled to the needle insertion mechanism 20 to provide the drive fluid 32 thereto in order to actuate the needle insertion mechanism 20.

The needle insertion mechanism 20 includes a needle 22 and/or a cannula 24 having a storage state where the needle 22 and/or the cannula 24 is retracted within the housing 12 and an operative state wherein a tip of the needle 22 and/or the cannula 24 is deployed through the opening 46. Upon activation of the drug delivery device 10, the drug delivery device 10 may enable, connect, or open necessary connections to establish fluid communication between the container 110 and the fluid conduit 18. Simultaneously or subsequently, the needle insertion mechanism 20 may insert the needle 22 into the patient 11. The needle 22 may be constructed of a material that is rigid or flexible. In examples where the needle 22 is rigid, the needle 22 may be made of a material that is more rigid and/or harder than the cannula 24. For example, the needle 22 may be made of metal and the cannula 24 may be made of plastic or another polymer. The relative flexibility of the cannula 24 may allow it to be disposed subcutaneously within the patient's tissue 11 for a period of a time without causing pain or discomfort to the patient. In examples where the needle 22 is flexible, the needle 22 may be constructed from a super-elastic material such as nitinol, a polymer, or another material that allows the needle 22 to follow a curved path without sustaining damage. In examples where both the needle 22 and cannula 24 are included, the needle 22 may function as a trocar for creating a pathway through the patient's tissue to facilitate insertion of the cannula 24. Immediately or shortly after insertion of the cannula 24, the needle 22 may be retracted back towards the housing 12 leaving the cannula 24 within the patient's tissue 11 for subcutaneous delivery of the drug 102. In other examples, the cannula 24 may be omitted and the needle 22 may remain within the patient's tissue after insertion for subcutaneous delivery of the drug. In still further examples, the needle 22 may be omitted and the cannula 24, which may be constructed of a non-metal material such as a polymer, may be inserted by itself into the patient's tissue 11 for subcutaneous delivery of the drug. After needle 22 and/or cannula 24 has been inserted, the activation mechanism 30, by releasing or pushing on the drive fluid 32, may force the drug or medicament 102 stored in the container 110 through the sterile fluid flow path 19 of the fluid conduit 18 and into the needle insertion mechanism 20 for subcutaneous delivery to the patient 11.

After the bottom wall 12b of the housing 12 is attached to the patient's skin 11, the needle insertion mechanism 20 may be activated to move a delivery member from a retracted position within the housing 12 to a deployed position extending outside of the housing 12. In the present embodiment, this may include the needle insertion mechanism 20 inserting the needle 22 and the cannula 24 through the septum 48 and into the patient's skin 11 and subcutaneous tissue 11, as illustrated in FIG. 1. Immediately or shortly thereafter, the needle insertion mechanism 20 may automatically retract the needle 22, leaving the distal open end of the cannula 24 inside the patient for subcutaneous delivery of the drug 102. The needle 22 may be solid and have a sharpened end for piercing the patient's skin 11, whereas the cannula 24 may be hollow and have a blunt end.

In some embodiments, the needle insertion mechanism 20 may be powered by the drive fluid 32 to selectively provide actuation energy. In these examples, and as illustrated in FIGS. 2-4, the drive fluid 32 enters a cylinder 25 having a first end 25a and a second end 25b. The cylinder 25 accommodates a piston 26 coupled to the needle 22 or cannula 24. A spring 28 is disposed in the cylinder 25 and exerts a biasing force on the piston 26 to initially retain the piston, and thus the needle or cannula 24, in a storage state where the needle 22 or cannula 24 are disposed within the housing 12. Upon activating the activation mechanism 30, the drive fluid 32 exerts an opposing force on the piston 26 to overcome the biasing force exerted by the spring 28 and urge the needle 22 or cannula 24 out of the housing for insertion into the patient's tissue 11 (see, e.g., FIG. 3).

In other examples, the needle insertion mechanism 20 may include one or more springs (e.g., coil springs, torsion springs, etc.) initially retained in an energized state, and which are released upon depression of the actuator 16 in order to insert the needle 22 and cannula 24 into the patient. Furthermore, retraction of the needle 22 may be achieved by the automatic release of another spring after the needle 22 and cannula 24 have been inserted into the patient. Other power sources for insertion and/or retraction are possible, including, for example, an electric motor, a hydraulic or pneumatic pump to provide actuation energy.

As previously noted, the container 110 includes the wall 112 having the interior surface 112a that defines the reservoir 114 that is filled with the drug 102, and additionally includes a first end 110a and a second end 110b. In some embodiments, the reservoir 114 may be pre-filled with the drug 102 by a drug manufacturer prior to installation of the container 110 in the drug delivery device 10. In some embodiments, the container 110 may be rigidly connected to the housing 12 such that the container 110 cannot move relative to the housing 12; whereas, in other embodiments, the container 110 may be slidably connected to the housing 12 such that the container 110 can move relative to the housing 12 during operation of the drug delivery device 10. The container 110 may have an elongate, barrel-like or cylindrical shape extending along a longitudinal axis A. In embodiments where the drug delivery device 10 is configured as an on-body injector, the longitudinal axis A of the container 110 may be perpendicular or substantially perpendicular, or otherwise non-parallel, to a direction in which the needle insertion mechanism 20 inserts a delivery member such as the cannula 24 into the patient 11. This configuration may allow the on-body injector to have a generally planar, low-profile shape that can be worn by the patient without impeding the patient's movement. Initially, the plunger 120 may be positioned in the container 110 at or near the second end 110b thereof. The plunger 120 may sealingly and slidably engage the interior surface 112a of the wall 112, and thus is movable relative to the wall 112. Put differently, the plunger 120 acts as a seal that restricts the drug 102 from exiting the second end 110b of the container 110.

The volume of the drug 102 contained in the reservoir 114 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 114 may be completely or partially filled with the drug 102. The drug 102 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

The pressure chamber 100 has a wall 101 that defines an interior surface 101a defining an interior volume 103 that accommodates the container 110 as well as the drive fluid 32. In some examples, upon actuation of the device 10, the drive fluid 32 enters the interior volume 103 of the pressure chamber 100 to not only expel the drug 102 from the container 110, but to also apply an equalizing pressure on an outer surface 112*b* of the wall 112 of the container 110. Examples of such arrangements are described in previously-noted U.S. App. No. 62/543,058, filed on Aug. 9, 2017, the entire contents of which are incorporated by reference herein. In other examples, the pressure chamber 100 may be pre-pressurized by a drive fluid prior to activation of the device 10. Examples of such arrangements are described in U.S. Appl. No. 62/875,709, filed on Jul. 18, 2019, the entire contents of which are incorporated by reference herein.

With reference to FIGS. 2-4, a first example relief mechanism 150 The relief mechanism 150 includes the relief chamber 160 having a first end 160*a*, a second end 160*b*, and an interior volume 161 and a movable member 162 disposed within the interior volume 161 of the relief chamber 160. In this example, the movable member 162 is in the form of a fluid piston movable between the first and second ends 160*a*, 160*b* of the relief chamber 160. FIG. 2 illustrates the relief mechanism 150 in a storage state. The movable member 162 may be biased towards the first end 160*a* of the relief chamber 160 via a resilient member 164 also disposed within the interior volume 161 of the relief chamber 160. In some examples, the movable member 162 may be biased towards the first end 160*a* of the relief chamber by advantageously allowing gravity to downwardly bias the movable member 162. Other examples are possible. In the illustrated example, the first end 160*a* of the relief chamber 160 is operably coupled to the fluid conduit 18. Further, the movable member 162 includes a coupling mechanism 166 to selectively engage and open the vent 152.

As previously noted, upon engaging the actuator 16, the activation mechanism 30 may release and/or urge the drive fluid 32. In the illustrated example, the drive fluid 32 enters into both the interior volume 103 of the pressure chamber 100 and the interior volume 113 of the container 110. With reference to FIG. 3, in a first operational state, the drive fluid 32 that enters the interior volume 113 of the container 110 exerts a force on the second end 120*b* of the plunger 120 that causes the plunger 120 to move towards the first end 110*a* of the container 110. In these examples, the force from the drive fluid 32 may be sufficient to shift the container 110 relative to the container access mechanism 130, which may cause the container needle 132 to pierce the septum 134, and thus create a flow path between the reservoir 114 and the fluid flow path 19. Also as previously noted, at this time, the drive fluid 32 may also urge the piston 26 disposed in the cylinder 25 from the first end 25*a* to the second end 25*b* to insert the needle 22 into the patient's tissue 11.

When the plunger 120 begins expelling the drug 102 from the reservoir 114, the drug 102 enters the fluid conduit 18 and is delivered to the patient's tissue 11 via a connection 49 between the fluid conduit 18 and the needle 22 (or in some examples, via the cannula 24). Further, the drug 102 in the fluid conduit increases a pressure exerted on the movable member 162 within the fluid conduit 18 due, in part, to a flow resistance of the needle 22. This fluid pressure generated by the drug 102 is sufficient to move the movable member 162 towards the second end 160*b* of the relief chamber 160 and fill the interior volume 161 with the drug 102, which in turn causes the coupling mechanism 166 to engage (e.g., become coupled to) the vent 152. In these examples, the coupling mechanism 166 may be in the form of a latch and groove arrangement, a magnetic coupling, or other similar arrangements that allow components to secure to each other.

With reference to FIG. 4, the drive fluid 32 will continue to push against the plunger 120 until the interior surface 122 of the plunger reaches the first end 110*a* of the container 110, upon which the drug 102 will be expelled from the container 110 and emptied from the fluid conduit 18. As a result, the fluid pressure within the fluid conduit 18 may substantially drop (e.g., to an approximately near-atmospheric value). The resilient member 164 may overcome this reduced (and/or nonexistent or near-nonexistent) fluid pressure to urge the movable member 162 back towards the first end 160*a* of the relief chamber 160, which in turn causes the coupling mechanism 166, now coupled to the vent 152, to open the vent 152. This urging by the movable member 162 also causes any remaining drug 102 in the interior volume 161 of the relief chamber 160 to be expelled therefrom.

At this time, any remaining drive fluid 32 contained within the pressure chamber 100 will be expelled therefrom until a pressure equilibrium is obtained between the interior volume 103 of the pressure chamber 100 an environment surrounding the pressure chamber (e.g., the inner volume 12*a* of the housing 12). Further, in some examples, at this time, the pressure vessel or other container 31 may be emptied, and as such, the spring 28 may overcome any remaining biasing force exerted on the piston 26 and move the piston 26 back to the first end 25*a* of the cylinder 25 which in turn will remove the needle 22 from the patient's tissue 11. In some examples, the housing 12 may also include an opening (not illustrated) to allow the drive fluid 32 to vent to an environment external to the housing 12.

FIGS. 5 and 6 illustrate a second example relief system 250 corresponding to the relief system 150 illustrated in FIGS. 2-4, and as such, includes similar features and operation of the relief system 150 that will not be discussed in substantial detail. In the illustrated example, the relief system 250 includes a movable member 262 in the form of a flexible membrane 262*a* and a piston 262*b* positioned at the first end 260*a* of the relief chamber 260. This flexible membrane 262*a* limits the amount of drug 102 that enters the interior volume 261 of the relief chamber 260 while still moving the piston 262*b* and the coupling mechanism 266 between the first and second ends 260*a*, 260*b* of the relief chamber 260.

It is also noted that in the example illustrated in FIGS. 5 and 6, the activation mechanism 30 is not directly coupled to the needle insertion mechanism 20. Rather, in this example, the force exerted on the plunger 120 by the drive fluid 32 is sufficient to cause the needle 22 to be inserted into the patient's tissue 11. However, in other examples, the activation mechanism 30 described with respect to FIGS. 2-4 may be used in the illustrated example of FIGS. 5 and 6.

FIG. 7 illustrates a third example relief system 350 corresponding to the relief systems 150 and 250 illustrated in FIGS. 2-6, and as such, includes similar features and operation of the relief systems 150 and 250 that will not be discussed in substantial detail. In the illustrated example, the relief system 350 additionally includes an overpressure relief mechanism in the form of a resilient member 359 operably coupled to the vent 352. The resilient member 359 exerts a biasing force on the vent 352 to initially retain the vent in a closed configuration. In the event that the force exerted on the vent 352 from the drive fluid 32 exceeds the biasing force exerted by the resilient member 359, the vent 352 will open and the drive fluid 32 will be vented until the pressure inside and outside of the pressure chamber equilibrate.

Turning to FIGS. 8-10, a more detailed depiction of the relief system 350 is provided. In FIG. 8, the device 10, and thus the relief system 350, is in a storage state, and includes a relief cylinder 360 having first and second ends 360*a*, 360*b*, an interior volume 361, a movable member 362 in the form of a flexible membrane 362*a* and a piston 362*b* positioned at the first end 360*a* of the relief chamber (in the storage state). A spring 364, also disposed within the relief cylinder 360, biases the movable member 362 towards the first end 360*b* of the relief cylinder 360. The piston 362*b* forms an opening 363 in the form of a slit or gap that accommodates a first end 370*a* of a latch hook 370. In some examples, the first end 370*a* of the latch hook 370 may be frictionally fit into the opening 363 formed in the piston 362*b*, and in other examples, coupling mechanisms such as fasteners, adhesives, and the like may be used. A second end 370*b* of the latch hook 370 includes a finger member 371.

The coupling mechanism 366 includes the latch hook 370, a rocker member 372, and a pressure retainer 380. The second end 360*b* of the relief cylinder 360 includes a support 360*c* extending therefrom having a mounting portion 360*d* in the form of a peg or similar member. The rocker member 372 includes a rotatable mounting portion 372*a* in the form of an opening that couples to the mounting portion 360*d* of the support 360*c* to rotatably mount the rocker member 372 relative to the relief cylinder 360. In other examples, the arrangements of the mounting portions on the rocker member 372 and the support 360*c* may be reversed, meaning the rocker member 372 may include a peg or similar member that is inserted into an opening formed on the support 360*c*. The rocker member 372 additionally includes a latch coupling region 374 and a retainer coupling region 376. In the illustrated example, the latch coupling region 374 and the retainer coupling region 376 are in the form of a groove or channel and can have varying dimensions, orientations, and/or configurations.

In this example, the vent 352 is in the form of a diaphragm 352*a* and a piston 352*b* in fluid communication with a vent conduit or pressurized gas line 354 that couples the pressure chamber 100 (not illustrated in FIGS. 8-10) to the relief system 350. The vent conduit 354 opens to a vent cylinder 351 having a first end 351*a*, a second end 351*b*, and a support 351*c* including a mounting portion 351*d* in the form of a peg or similar member. In the illustrated example, the vent cylinder 351 and the relief cylinder 360 are integrally formed in a single housing, but in other examples, the vent cylinder 351 and the relief cylinder 360 may be separately formed.

The pressure retainer 380 includes a rotatable mounting portion 380*a* in the form of an opening that couples to the mounting portion 351*d* of the support 351*c* to rotatably mount the pressure retainer 380 relative to the vent relief cylinder 351. In other examples, the arrangements of the mounting portions on the pressure retainer 380 and the support 351*c* may be reversed, meaning the pressure retainer 380 may include a peg or similar member that is inserted into an opening formed on the support 351*c*. The pressure retainer 380 additionally includes a rocker coupling region 382 and a spring retaining region 384. In the illustrated example, the rocker coupling region 382 and the spring retaining region 384 are in the form of a protrusion and an opening, respectively, and can have varying dimensions, orientations, and/or configurations.

The flexible membrane 352*a* and the piston 352*b* are disposed within the vent cylinder 351 and are biased towards the first end 351*a* thereof by a spring 358 having a first end 358*a* disposed within the piston 352*b*. A second end 358*b* of the spring 358 is further disposed within the spring retaining region 384 of the pressure retainer 380. In the storage state illustrated in FIG. 8, the rocker coupling region 382 is disposed within the retainer coupling region 376, and as such, the spring retaining region 384 retains the spring 358 in an energized state that in turn biases the piston 352*b* and the flexible membrane 352*a* into sealing engagement with the vent conduit 354. It will be appreciated that the spring 358 illustrated in FIGS. 8-10 may correspond to the resilient member 359 illustrated in FIG. 7, as both components exert a biasing force on the flexible membrane 352*a*.

In the first operative state illustrated in FIG. 9, the drug 102 enters the fluid conduit 18, and fluid pressure within the fluid conduit 18 urges the diaphragm 362*a* and the piston 362*b* towards the second end 360*b* of the relief cylinder 360. This movement compresses the spring 364, and additionally moves the finger member 371 of the latch hook 370 into engagement with the latch coupling region 374 of the rocker member 372. The finger member 371 may be constructed from a flexible material that flexes upon contacting the rocker member 372 until snapping into the latch coupling region 374. During the first operative state, the drive fluid 32 enters the vent conduit 354 and exerts an urging force on the flexible membrane 352*a*, but the pressure retainer 380 continues to retain the spring 358, the piston 352*b*, and the flexible membrane 352*a* in sealing engagement with the vent conduit 354.

If the device 10 becomes over pressurized, the drive fluid 32 may exert a greater force on the flexible membrane 352*a* than the opposing force exerted by the spring 358. As a result, the vent 352 may open, meaning the flexible membrane 352 ceases to seal the vent cylinder 351, thus allowing the drive fluid 32 to be vented until the force exerted by the spring 358 is greater than the force exerted by the drive fluid 32, at which point the flexible membrane 352*a* is again moved into sealing engagement. In some examples, the dimensions of the spring 358 and the flexible membrane 352*a* may be chosen such that if the pressure from the drive fluid 32 rises above approximately 100 psi, the flexible membrane 352*a* will lift and allow the drive fluid 32 to escape. Other examples are possible.

As illustrated in FIG. 10, upon completion of drug delivery, the fluid pressure in the fluid conduit 18 drops to a zero or near-zero value, and as described in the previous examples, the spring 364 biases the piston 362*b* and the flexible membrane 362*a* to the first end 360*a* of the relief cylinder 360. Movement of the piston 362 causes the latch hook 370 to also move towards the first end 360*a* of the relief cylinder 360, and because the finger member 371 is coupled to the rocker member 372 via the latch coupling region 374, the rocker member 372 rotates about the mounting portion 360*d* of the support 360*c*. The rotation of the rocker member 372 disengages the rocker coupling region 382 of the pressure retainer 380 from the retainer coupling region 376 of the rocker member 372. As a result, the spring 358 urges the pressure retainer 380 to rotate about the mounting portion 351*d* and away from the first end 351*a* of the vent cylinder 351, thus removing the biasing and sealing force on the piston 352*b* and the flexible membrane 352*a*. As a result, the vent 352 opens to expel the drive fluid 32.

So configured, the relief systems and mechanisms described herein more safely remove remaining drive fluid from the pressure chamber, thereby providing more safety by reducing a likelihood of the device becoming over pressurized.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti- TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:

a housing adapted to be releasably coupled with a patient;

a pressure chamber disposed in the housing and including a vent;

a container at least partially disposed in the pressure chamber for storing a drug and connectable in fluid communication with a fluid conduit;

an activation mechanism adapted to release a pressurized drive fluid into the pressure chamber for expelling the drug from the container into the fluid conduit; and a relief mechanism operably coupled to the fluid conduit and adapted to open the vent to release the pressurized drive fluid from the pressure chamber in response to a change in pressure in the fluid conduit, wherein the relief mechanism includes a relief chamber having a first end and a second end, the relief chamber being operably coupled to the fluid conduit and including a movable member movable between the first end and the second end of the relief chamber and being biased towards the first end of the relief chamber, wherein upon engaging the activation mechanism, the drug in the fluid conduit urges the movable member from the first end of the relief chamber to the second end of the relief chamber to operably couple the relief mechanism to the vent.

2. The drug delivery device of claim 1, further comprising a resilient member coupled to the movable member to bias the movable member towards the first end of the relief chamber.

3. The drug delivery device of claim 1, wherein upon completion of delivery of the drug, the movable member moves towards the first end of the relief chamber and opens the vent to remove the pressurized drive fluid from the pressure chamber.

4. The drug delivery device of claim 1, further comprising an insertion mechanism configured to be operably connected and in fluid communication with the container via the fluid conduit, the insertion mechanism including at least one of a needle or a cannula to be inserted into the patient for delivering the drug to the patient.

5. The drug delivery device of claim 1, further comprising a container access mechanism at least partially disposed within the housing and being operably coupled to at least one of the pressure chamber or the container, the container access mechanism comprising:

a needle or a cannula; and a sterile barrier disposed proximal to the needle or cannula in a first configuration where the sterile barrier is intact.

6. The drug delivery device of claim 5, wherein upon engaging the activation mechanism, relative movement between the needle or cannula and the sterile barrier causes the needle or cannula to pierce the sterile barrier to create the fluid conduit allowing the drug to be expelled from the container.

7. The drug delivery device of claim 1, further comprising an overpressure relief mechanism operably coupled to the relief mechanism to release the pressurized drive fluid from the pressure chamber when a pressure within the pressure chamber exceeds a predetermined value, wherein the overpressure relief mechanism optionally includes a resilient member adapted to exert an opposing force on the vent.

8. The drug delivery device of claim 1, wherein the movable member comprises at least one of a fluid piston or a diaphragm.

9. The drug delivery device of claim 1, wherein the pressurized drive fluid comprises at least one of a pressurized gas or a pressurized liquid.

* * * * *